(12) United States Patent
Okinishi

(10) Patent No.: US 7,188,951 B2
(45) Date of Patent: Mar. 13, 2007

(54) OPHTHALMOLOGIC APPARATUS

(75) Inventor: Satoru Okinishi, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 414 days.

(21) Appl. No.: 10/798,809

(22) Filed: Mar. 10, 2004

(65) Prior Publication Data

US 2004/0189937 A1 Sep. 30, 2004

(30) Foreign Application Priority Data

Mar. 11, 2003 (JP) ............................. 2003-065084

(51) Int. Cl.
*A61B 3/14* (2006.01)
(52) U.S. Cl. .................................. 351/206
(58) Field of Classification Search ................ 351/205, 351/206, 210, 213
See application file for complete search history.

(56) References Cited

U.S. PATENT DOCUMENTS

| | | | |
|---|---|---|---|
| 5,291,231 A | 3/1994 | Hideshima et al. | |
| 5,341,180 A | 8/1994 | Isogai et al. | |
| 5,822,446 A | 10/1998 | Kato | |
| 6,478,424 B1 * | 11/2002 | Grinvald et al. | 351/206 |

FOREIGN PATENT DOCUMENTS

JP 2002-229968 8/2002

OTHER PUBLICATIONS

Chinese Office Action mailed Jul. 7, 2006.

* cited by examiner

*Primary Examiner*—Timothy Thompson
(74) *Attorney, Agent, or Firm*—Morgan & Finnegan, LLP

(57) ABSTRACT

Photographic conditions of a plurality of retinal images photographed in one photographing routine are recorded in relation to the photographed images, respectively. Any image is selected from the plurality of images as a reference image, and using the photographic condition of the reference-image as a reference, a correction is made so that other images are expressed as images equivalent to an image photographed under the photographic condition of the reference image.

5 Claims, 13 Drawing Sheets

OPHTHALMOLOGIC APPARATUS

BACKGROUND OF THE INVENTION

1. Field of the Invention

The present invention relates to an ophthalmologic apparatus.

2. Related Background Art

In the ophthalmologic medical field, fluorescent contrast photography or image pickup is widely conducted in which a fluorescent contrast medium is injected through a vein of a subject into an anterior or retinas and choroids. The fluorescent contrast medium injected into the vein of the subject reaches a subject eye via blood circulation. At first, the fluorescent contrast medium is gradually concentrated in the subject eye as time passes. After reaching a maximum level, the concentration of the fluorescent medium in the subject eye gradually decreases due to absorption and excretion by circulation in the body. That is, in fluorescent contrast photography, in principle, a photograph site becomes rapidly bright from a dark state, and then gradually darkens, as time passes after injection of the fluorescent medium.

In fluorescent contrast photography, the variations in brightness described above are important information for understanding the states of circulation of the body fluid in the eye and the body. Accordingly, the illuminating light intensity and the exposure conditions and sensitivity of photographing means-are not usually changed at the time of fluorescent contrast photography.

A silver halid film is mainly used as photographing means, but in recent years, electronic image photography using a CCD or the like has been performed (Japanese Patent Application Laid-Open No. H10-260487).

In the example of the conventional technique described above, however, the brightness of the subject changes rapidly with time. Photography using a conventional silver halid film has a wide latitude (exposure allowable range), thus making it possible to photograph an image having no problems in practice with respect to a change in brightness when the subject is being photographed.

However, electronic image pickup means has a latitude smaller than that of the silver halid film, so that the photographed image may be too dark with respect to a change in brightness of the subject, or the brightness may be saturated. Thus, for obtaining an appropriate image, a gain (signal amplification factor) or the illuminating light intensity must be changed but consequently, important information, i.e., a change in brightness of the subject described above, is lost, and the image thus obtained is very difficult to use for diagnosis for circulation.

SUMMARY OF THE INVENTION

The object of the present invention is to solve the problems described above and to provide an ophthalmologic apparatus capable of obtaining an image with proper exposure.

The ophthalmologic apparatus according to the present invention for achieving the above object corrects an image group consisting of a plurality of images photographed while changing photographic conditions, using each of the photographic conditions of images in the image group, so that the image in the image group is expressed as an image photographed under predetermined photographic conditions.

Furthermore, the photographic conditions include at least one type of information of an amplification factor of image pickup means, the illuminating light intensity for a subject eye, and the intensity of transmitted photographing light of means for adjusting the intensity of photographing light reaching the image pickup means.

Further objects and configurations of the present invention will be apparent in embodiments described later.

DESCRIPTION OF THE PREFERRED EMBODIMENTS

The present invention will be described in detail based on embodiments shown in figures.

Figure 1:
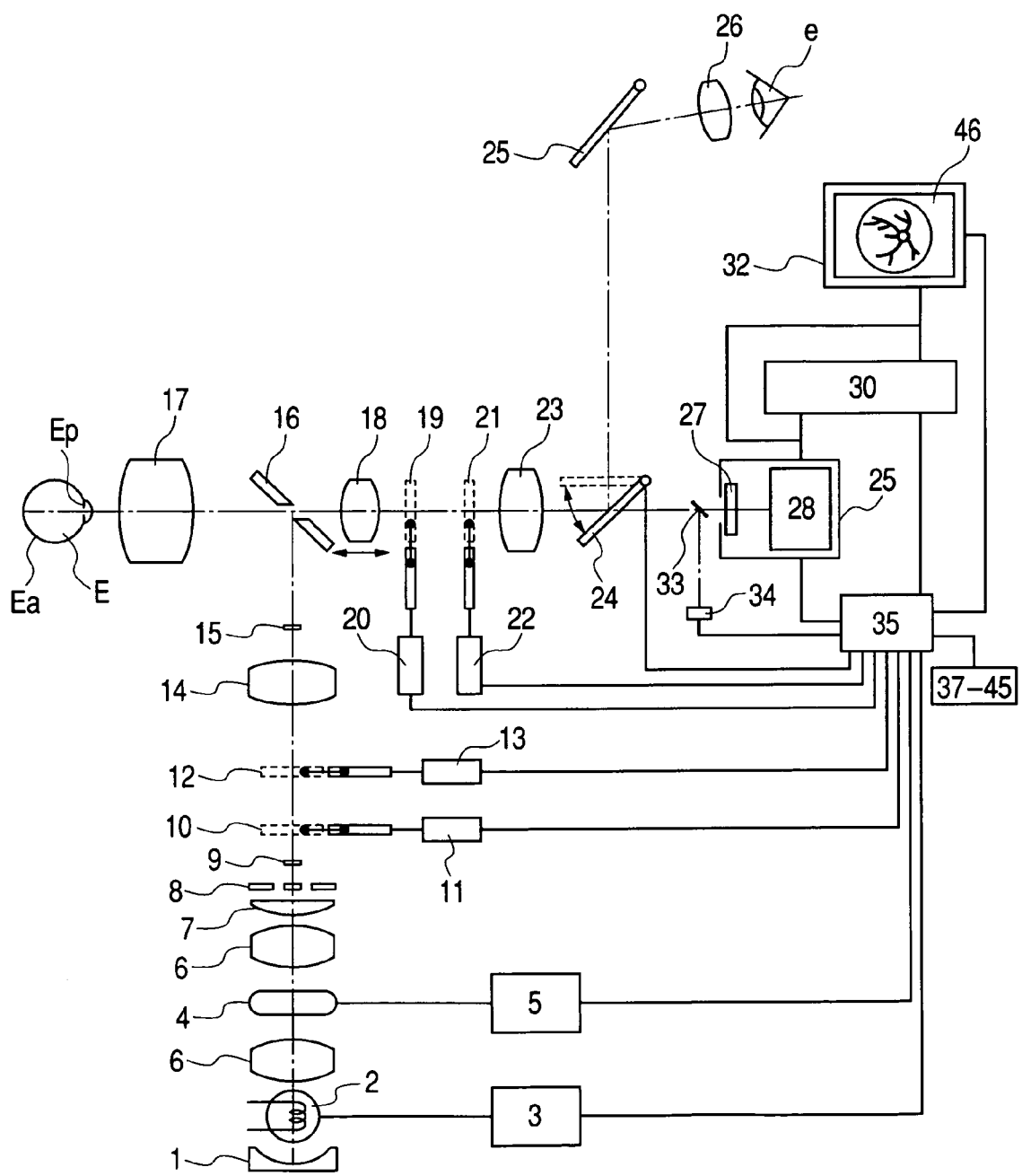
FIG. 1 is a block diagram of an apparatus.

FIG. 1 is a block diagram of a photographing apparatus. Illuminating light emitted from a lamp 2 of a continuous light emission source emission-controlled by continuous illumination light source control means 3 and a stroboscopic tube 4 of a stroboscopic illuminating light source emission-controlled by stroboscopic light source control means 5 passes through a condenser lens 6, and is formed into a ring shape by a field lens 7 and a ring slit 8. The illuminating light formed into a ring shape passes through a relay lens 14 and detrimental light blocking members 9 and 15, is reflected by a perforated mirror 16, passes through an objective lens 17, and is applied to a subject eye E. A photographic portion is illuminated by the illuminating optical system. The continuous illuminating light source control means 3 and the stroboscopic light source control means 5 receives indications of the intensity of emitted light, light emission timing, light emission time and the like, and performs of predetermined light source control.

Light reflected from the subject eye E passes through again the objective lens 17, holes of the perforated mirror 16, a focus lens 18 movable along the optical axis, and an image formation optical system 23 to a flap mirror 24 installed in such a manner that it can be freely inserted into/removed from a light path by a known drive means (not shown) operationally controlled by control means 35. If the flap mirror 24 is present in the light path, the light reflected from the subject eye E reaches a mirror 25, passes through a finder optical system 26, and forms an image on the pupil of eye e of the subject, so that the subject eye E to be examined can be visually observed.

If the flap mirror 24 is absent from the light path, the light reflected from the subject eye E reaches image pickup means 29 constituted by an electronic image pickup device 27 and image signal amplifying means 28, and forms an image on the electronic image pick up device 27, and an image signal output thereof is subjected to signal amplification processing in a predetermined gain (signal amplification factor) by the image signal amplifying means 28, sent to image process recording means 30 via known electric connection, and stored as an image. At the same time, it is sent to an image display apparatus 32 to provide display.

The image display apparatus 32 is under control by the control means 35, and is controlled for selection between display modes, and an input from the image pickup means 29 and an input from the image process recording means 30 are selectively displayed.

Furthermore, a transparent touch sensor 46 is installed on the display screen of the image display apparatus 32, and if a position on the display screen is selected by a subject, the position information is inputted to the control means 35.

The image signal amplifying means 28 can select a gain by control from the control means 35. Furthermore, the light reception state of the electronic image pickup device 27 and the gain of the image signal amplifying means 28 can be monitored by the control means 35 via the image signal amplifying means 28.

Further, a spectral mirror 33 for taking part of photographing light is installed in a photographing light path, and a light intensity sensor 34 is installed at the tip of the spectral light path. An output of the light intensity sensor 34 is inputted to the control means 35 and monitored as an indicator of a light exposure value of the electronic image pickup means 27. The control means 35 can automatically control light source light intensity control functions of the continuous illuminating light source control means 3 and the stroboscopic light source control means 5 based on an input signal from the light intensity sensor 34 and the gain of the image signal amplifying means 28.

In the illuminating optical system, a visible fluorescent exciter filter 10 for visible fluorescent contrast photography and an infrared fluorescent exciter filter 12 for infrared fluorescent contrast photography are installed in such a manner that they can be inserted into/removed from the light path by drive means 11 and 13 such as solenoids operationally controlled by the control means 35, respectively. Similarly, in an image pickup optical system, a visible fluorescent barrier filter 19 for visible fluorescent contrast photography and an infrared fluorescent barrier filter 21 for infrared fluorescent contrast photography are installed in such a manner that they can be inserted into/removed from the light path by drive means 20 and 22 such as solenoids operationally controlled by control means 32, respectively. The exciter filter has the job of extracting only exciting light for causing a predetermined fluorescent contrast medium to generate fluorescence from illuminating light. The barrier filter has the job of blocking only exciting light of fluorescent light and reflected exciting light from the eye to be tested. These jobs are same for visible light and infrared light.

In the case of a visible fluorescent photographing mode, the control means 35 inserts at least any one of the visible fluorescent exciter filter 10 and the visible fluorescent barrier filter 19 into the light path.

In the case of an infrared fluorescent photographing mode, the control means 32 inserts at least any one of the infrared fluorescent exciter filter 12 and the infrared fluorescent barrier filter 21 into the light path.

In the case of a color photographing mode, none of the above filters is inserted into the light path. Selection between the photographing modes described above is performed by the control means. 35 according to an input from mode selection inputting means 39.

Figure 2:
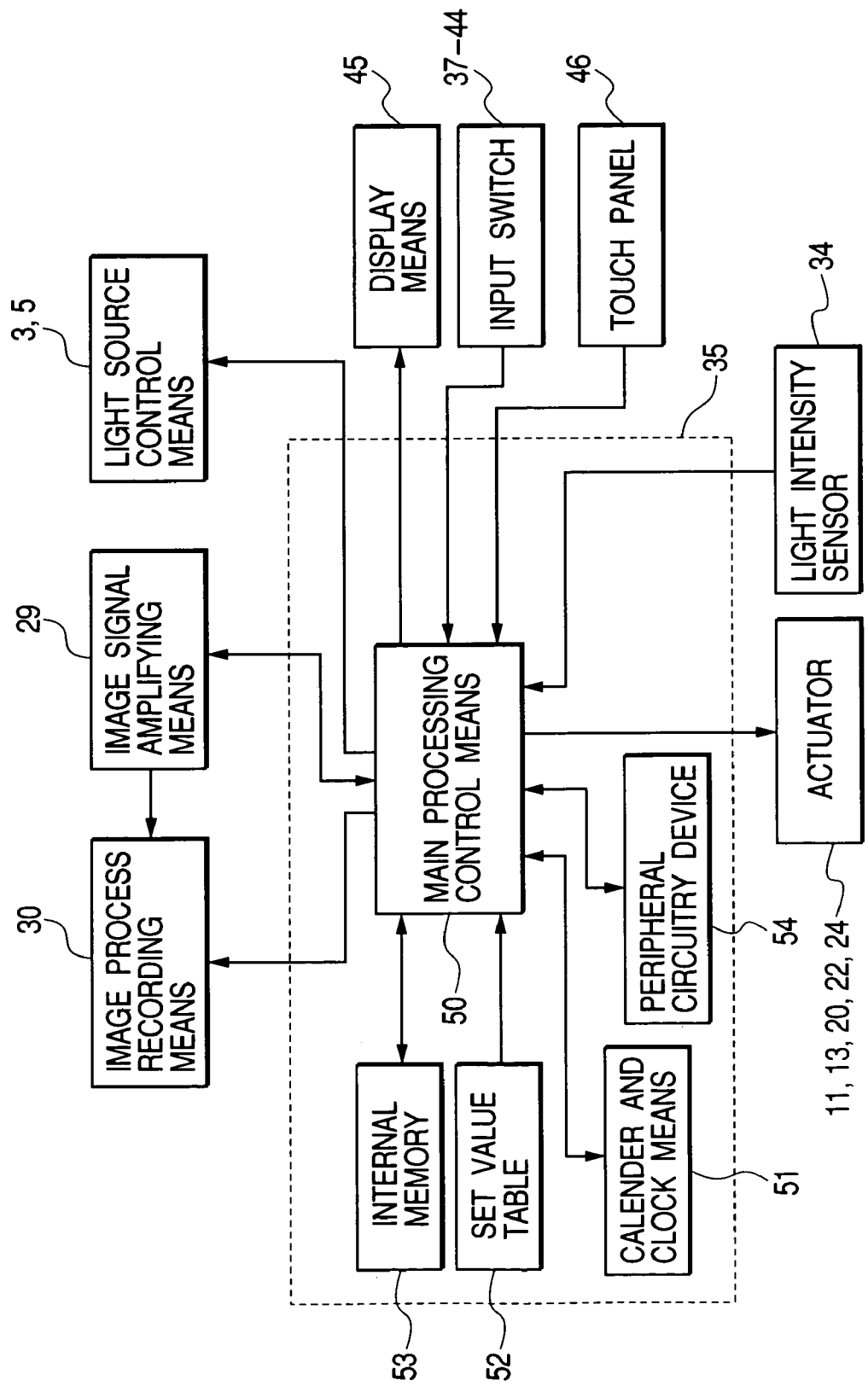
FIG. 2 is an explanatory view of control means.

As shown in FIG. 2, the control means 35 is comprised of main processing control means 50 performing control of operations of parts of the apparatus, control of operational modes, calculation processing, determination on a situation, and the like, calendar and clock means 51 ticking the date (year, month and day) and the time, a set value table 52 storing set values concerning apparatus control such as light intensity tables, gamma characteristics γc of the image pickup device 28 and gamma characteristics γc of the display means 32, an internal memory 53 temporarily storing external input values, set values read from a set value, results of calculation and the like, times of input of data and times of processing of data, and a peripheral device 54 supporting the main processing control means 50.

The main processing control means 50 establishes electric connection with light intensity control means 35, image signal amplifying means 28, image recording means 30, image processing means 31, actuators 11, 13, 20, 22 and 24 and the like to perform predetermined control. Furthermore, the main processing control means 50 changes the contents of the parts upon reception of inputs from input means 37 to 44 and a touch panel 46, and inputs predetermined information to the image recording means 30 and the image processing means 31. Furthermore, it displays predetermined control information and input information on the display means 45.

Figure 3:
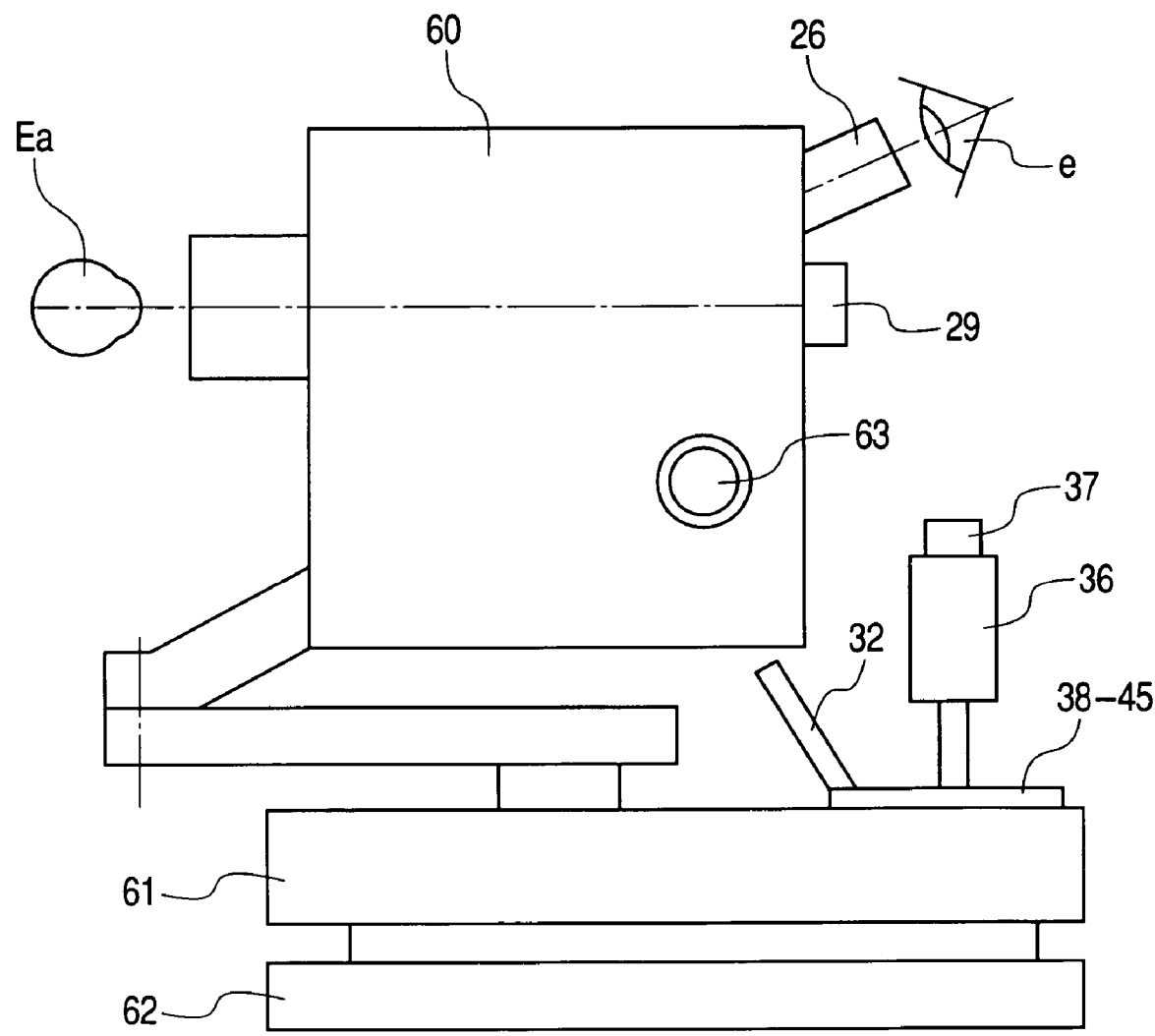
FIG. 3 is an outline view of the apparatus.

FIG. 3 is an outline view of an ophthalmologic photographing apparatus in this embodiment. A photographing apparatus main body 60 is installed on a movable stage 61, and can freely move vertically, longitudinally and laterally within a structural movable range with respect to the subject eye Ea by manipulating a manipulation knob 36. Image pickup means 29 and a focus adjustment knob 63 are installed in the photographing apparatus main body 60. Image display means 32, the manipulation knob 36, a photographing switch 37 mounted thereon, a group of input means 38 to 44 and display means 45 are installed on the movable stage 61.

Figure 4:
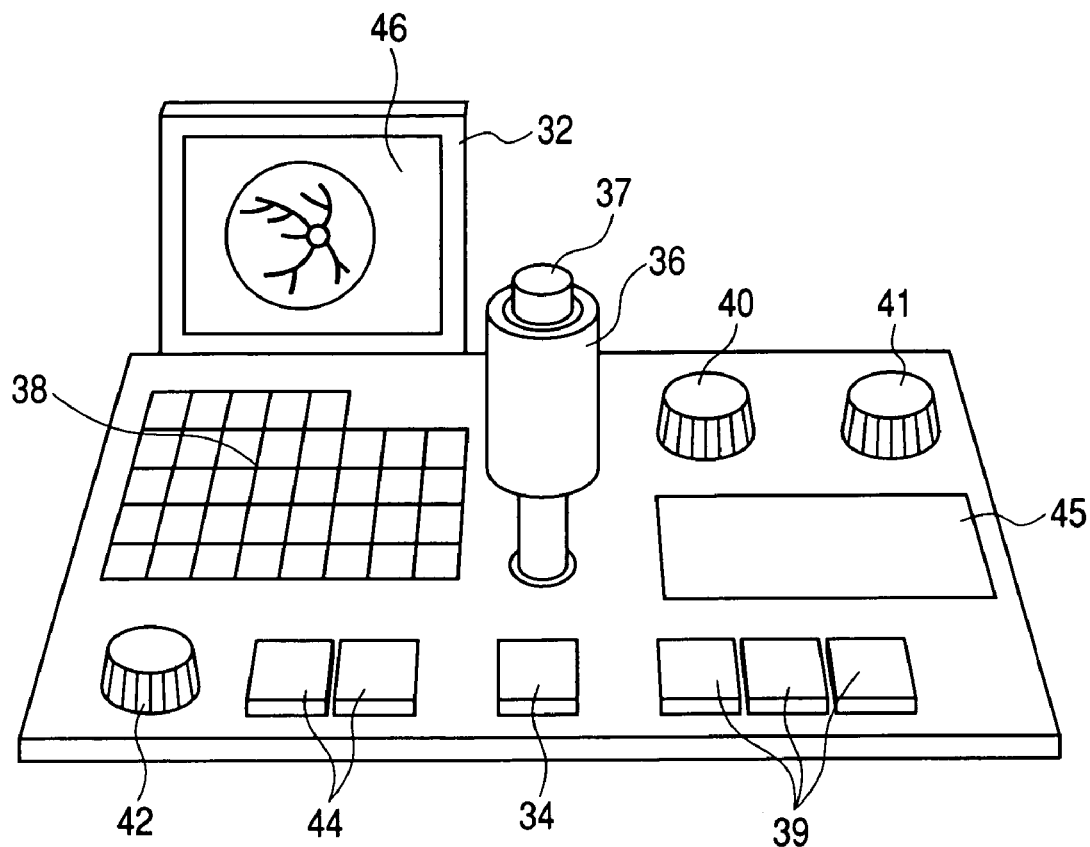
FIG. 4 is an explanatory view of a group of input means.

FIG. 4 shows the group of input means installed on the movable stage 61. The photographing switch 37 is installed on the manipulation knob 36. When the photographing switch 37 is pressed (ON), the stroboscopic tube 4 emits light, and in synchronization with the light emission, the electronic image pickup means 29 photographs an image of a predetermined site of the subject eye illuminated with stroboscopic light.

A keyboard switch 38 for inputting characters such as subject IDs and complicate settings for image processing and the like is provided on an operation panel, a plurality of subject IDs can be stored at a time in the control means 35, and the switch can be made between subject IDs by operating the keyboard switch 38. Mode switching input means 39 for switching between photographing modes, a lamp adjustment dial 40 for setting the light intensity of the continuous illuminating light source 2, a stroboscopic adjustment dial 41 for setting the light intensity of the stroboscopic illuminating light source 4, a gain dial 42 for setting a fixed gain of the image signal amplifying means 28, a timer switch 43 inputting to the control means 35 a signal marking a specific time at which the switch is pressed, a filter switch 44 for inserting the exciter filters and the barrier filters into the light path and removing the same from the light path according to the photographing mode, and display means 45 displaying the gains of the timer and the image signal amplifying means 28, illuminating light intensity, the photographing mode and the like are installed.

Figure 5:
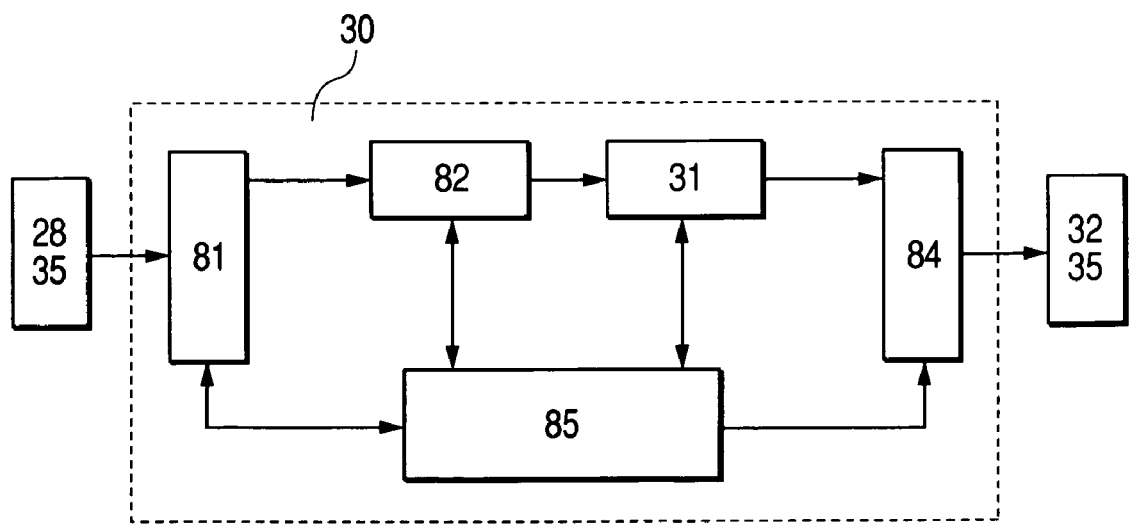
FIG. 5 is a block circuitry diagram of image process storing means.

FIG. 5 is a block circuitry diagram of the image process recording means 30, in which control signals and data are received by an input port 81, the data is temporarily stored in temporary storage means 82 such as a solid memory, and the control signal is inputted to a CPU 85. The CPU 85 controls the overall image process recording means 30, processes data stored in the temporary storage means 82 and permanent storage means 31 such as a hard disk. From an output port 84, data, the control signal and the like processed by the CPU are outputted to outside.

When the subject eye is photographed with the above configuration, processing and operations are performed as described below. Before photographing the subject eye, a photographing mode such as the visible fluorescent contrast photographing mode or infrared fluorescent contrast photographing mode is set by the mode switching input means 39. A desired gain Gn is set by the gain dial 42, the subject eye Ea is aligned, and then a fluorescent contrast medium is intravenously injected into the subject. In synchronization with the intravenous injection, the timer switch 43 is pressed to input a timer start time t0 to the control means 35. The control means 35 continues to subtract the start time t0 from a time Tn ticked by the calendar and clock means 51 to calculate time tn from the timer start. The time tn is inputted to the image process recording means 30 for adding the time tn to an image Pn photographed after the timer start.

A photographic site is observed with the finder optical system 26 while the photographing switch 37 is pressed to photograph the site. At this time, the control means 35 compares the light exposure value monitor and the intensity of emitted light of the electronic image pickup means 27 by input from the light intensity sensor 34 with the gain Gn of the image signal amplifying means 28 as described previously to make a setting automatically so that the intensity of emitted light becomes an appropriate light intensity Fn of the stroboscopic tube 4 via the stroboscopic light source control means 5. A plurality of images Pn is photographed while changing the gain Gn as necessary. The photographing mode, the gain Gn and the light intensity Fn set as described above are temporarily stored in the internal memory 53 in the control means 35 while they are set.

At the time when the photographing of the image Pn is ended, the image Pn outputted from the amplifying means 28 is captured in the temporary storage means 82 via the input port 81 of the image process recording means 30 shown in FIG. 5. At the same time, information of the photographing mode, gain Gn, light intensity Fn and timer time tn stored in the internal memory 53 in the control means 35 is similarly captured in the temporary storage means 82 via the input port 81.

The CPU of the image process recording means 30 carries out processing for adding photographic condition parameters such as the photographing mode, the gain Gn, the light intensity Fn and the timer time tn to the image Pn recorded in the temporary storage means 82, and records the image Pn in the permanent storage means 31 as one image of the image group So. n is any natural number, n=1→d→m.

At the time when the photographing of the subject in this photographing mode is ended, pressing the timer switch 43 again causes the control means 35 to stop the timer to end the capturing and recording of images belonging to the image group So in the image process recording means 30.

Figure 6:
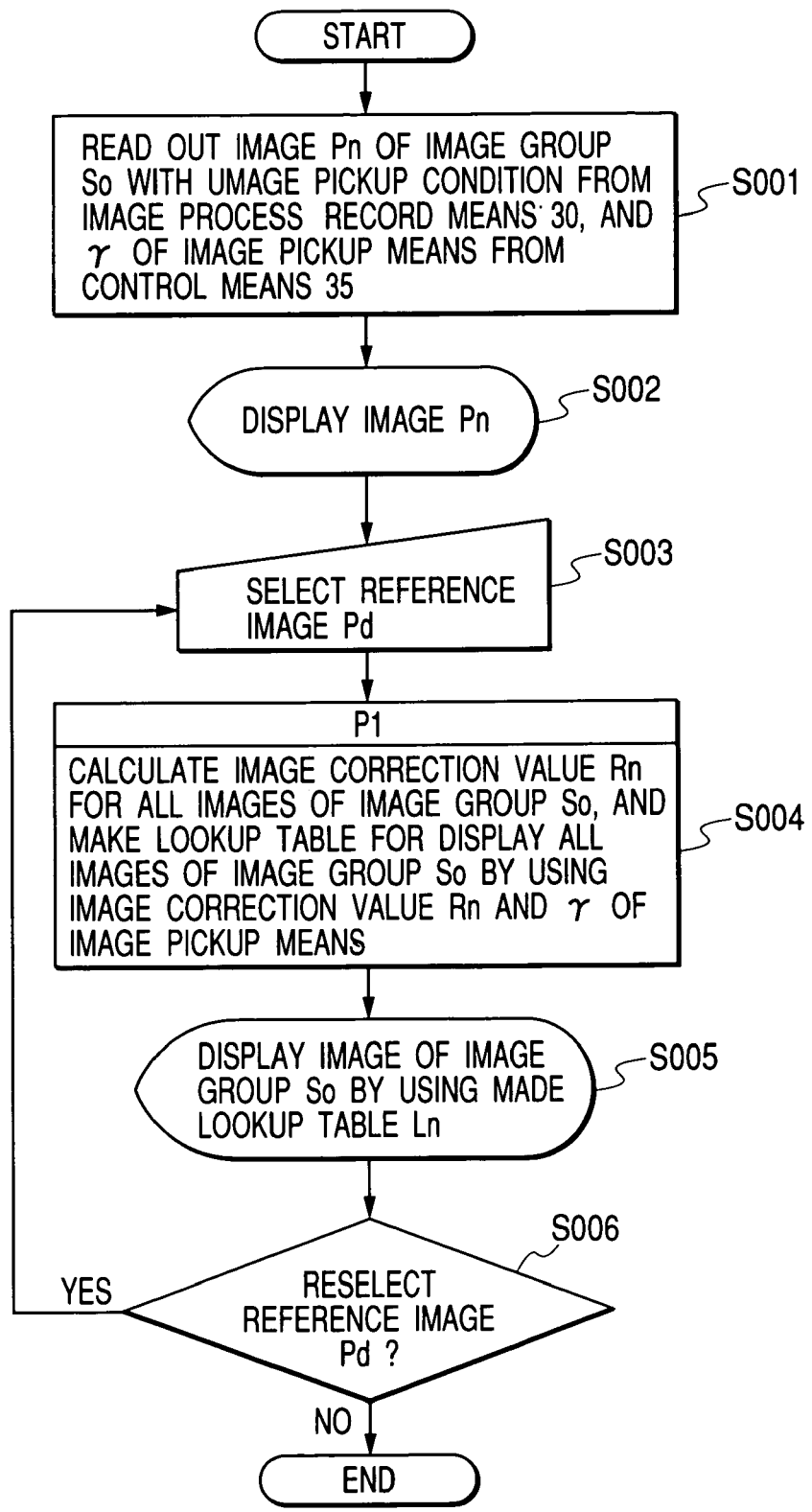
FIG. 6 is a flowchart diagram of processing.

Details of image processing will be described below according to the flowchart shown in FIG. 6.

S001: When an image processing command is inputted to the image process recording means 30 from the control means 35, m images Pn in the image group So recorded in the permanent storage means 31 and accompanying data of photographic conditions and the like are written in the temporary storage means 82. At the same time, the gamma γc of the image pickup means 27 is read in the temporary storage means 82 from the control means 35.

Figure 7:
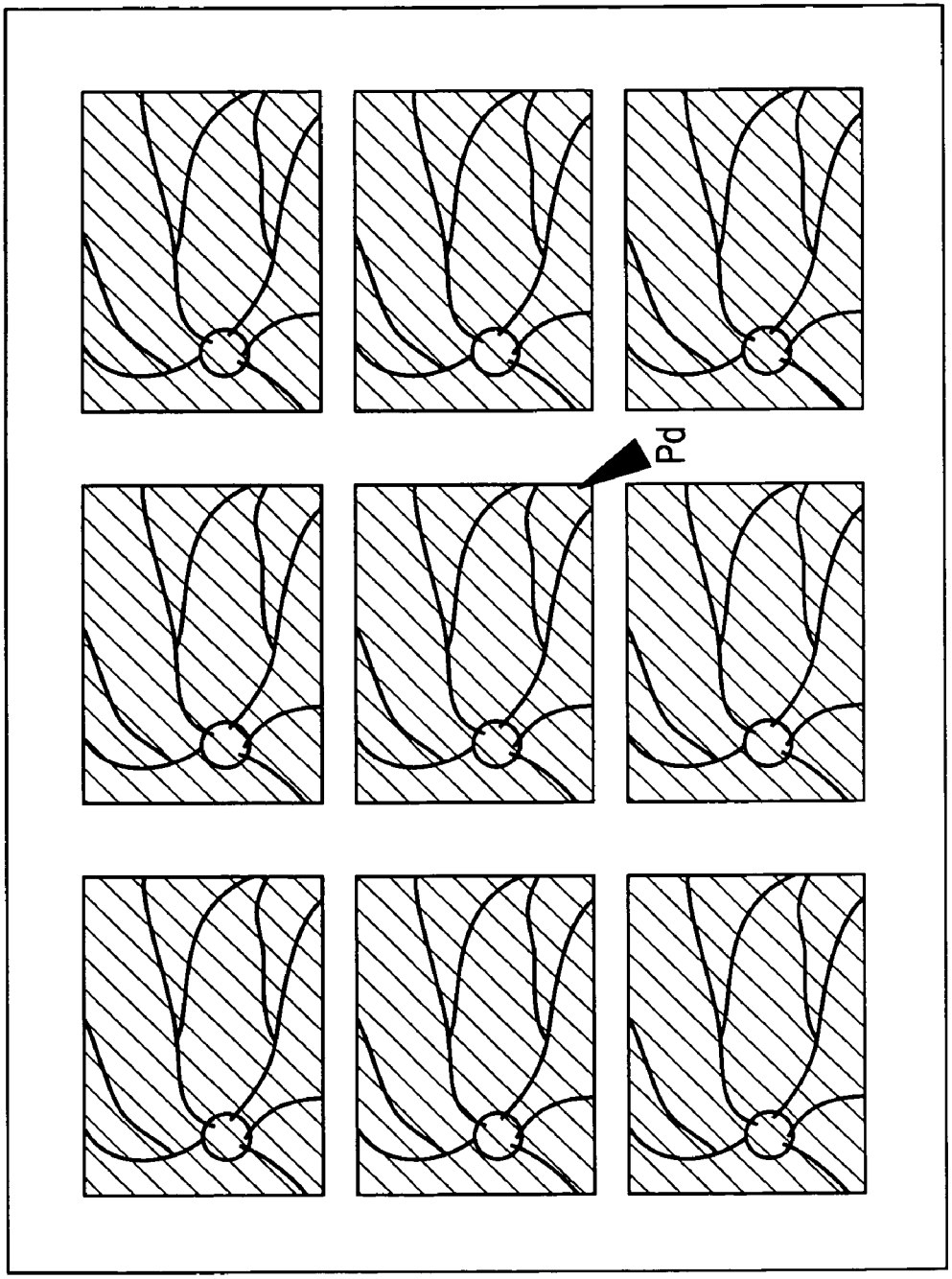
FIG. 7 shows an example of display of images in an image group So.

S002: The data read in the temporary storage means 82 is converted into images by the CPU 85 shown in FIG. 5, and some of them are displayed on the image display means 32 as shown in FIG. 7. The images displayed at this time have equal are displayed in equal brightness. In this example, the subject becomes darker with time, but may become brighter or cyclically brighter and then darker, and in any case, it can be considered that the same holds true.

S003: When the examiner designates an image to be selected as a reference image, the touch sensor 46 on the display screen of the image display apparatus 32 inputs a position on the display screen indicated by the examiner in the image process recording means 30 via the control means 35, and the image process recording means 30 recognizes an image displayed at this position and determines the image as a reference image Pd.

In the image process recording means 31, image processing is carried out as described below, whereby the image Pn can be expressed as an image photographed under conditions of the light intensity Fd and gain Gd same as those for the image Pd.

S004: A function for comparing the light intensities Fd and Fn to convert the result into an image correction value is determined to be f1 (Fd, Fn), and a function for comparing the gains Gd and Gn to convert the result into an image correction value is determined to be f2 (Gd, Gn).

In this embodiment, attention is given to the intensity of received light at the light receiving surface of the image pickup device 27 at the time of photographing the image Pd for the image Pn, and the functions f1 is defined as functions for determining the ratio of brightness of the images as follows. Since the intensity of received light at the light receiving surface of the image pickup device 27 is proportional to the intensity of emitted light of the illuminating light source, the functions f1 (Fd, Fn) are expressed by following equation:

$$f1(Fd, Fn)=Fn/Fd \quad (1)$$

For the function f2 (Gd, Gn), the gains Gd and Gn usually have a dB as a unit, and the amount of amplification E/Eo of the gain Go is defined as follows:

$$E/Eo=10^{(Go/20)} \quad (2)$$

Since the ratio of the intensity of received light at the light receiving surface of the image pickup device 27 can be considered as the ratio of the amount of amplification, the function f2 is expressed by the following equation:

$$f2(Gd, Gn)=\{10^{(Gn/20)}\}/\{10^{(Gd/20)}\} \quad (4)$$

The image correction value Rn of the image Pn for the image Ph is expressed by the following equation:

$$Rn=f1(Fn, Fd) \times f2(Gn, Gd)=(Fn/Fd) \times \{10^{(Gn/20)}\}/\{10^{(Gd/20)}\} \quad (5)$$

Figure 8:
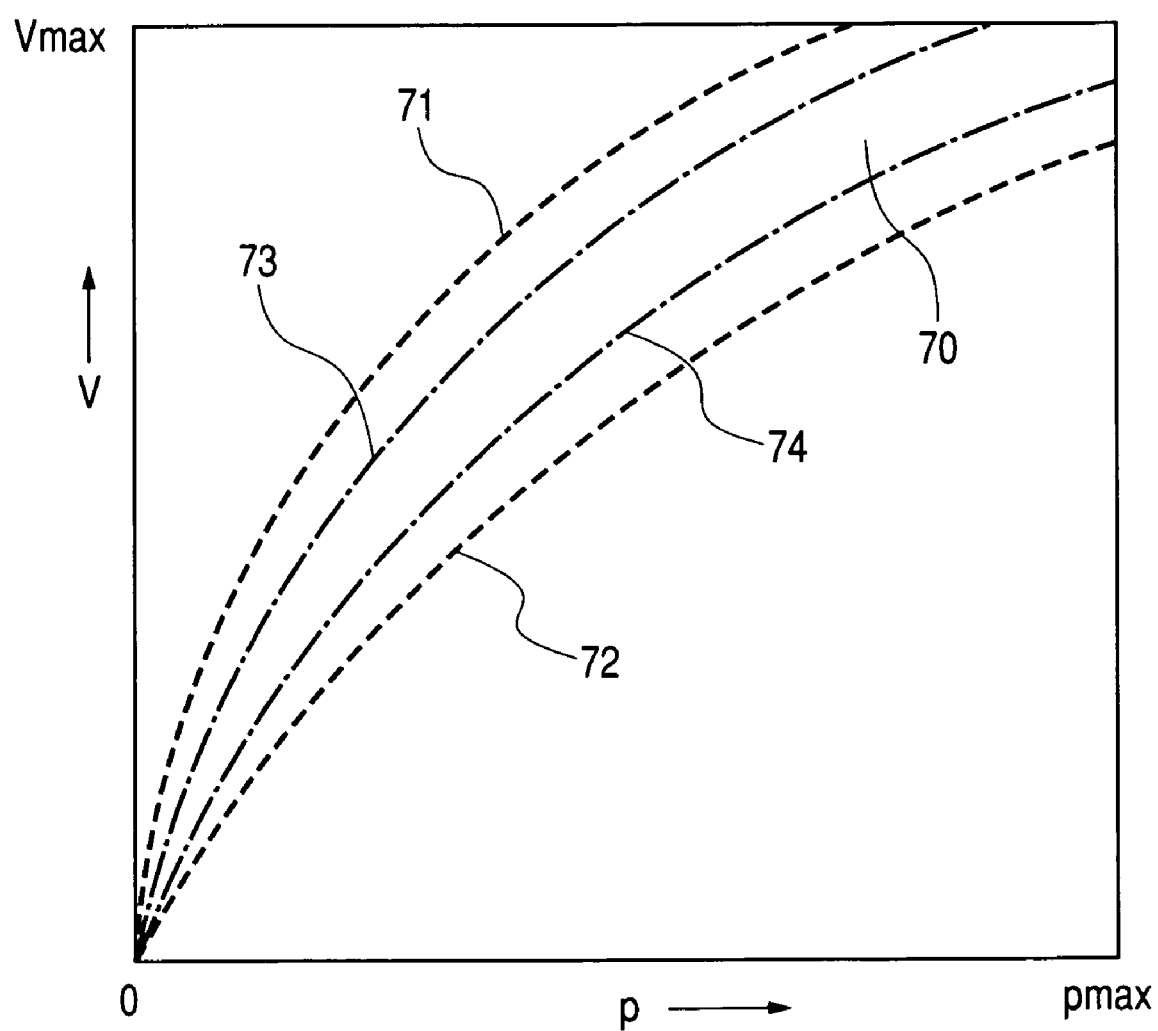
FIG. 8 is a lookup table of an image Pn.

The lookup table of the image Pn has characteristics 70 of FIG. 8. The relation between the input V and the output p in the characteristics 70 is expressed by the following equation:

$$V=a \times (p^{\gamma c}) : a=1/pmax \quad (6)$$

The right side in the equation is multiplied by the correction value Rn calculated by the equation (5) to obtain the following equation:

$$V = Rn \times a \times (p \char`\^ \gamma c) \qquad (7)$$

Figure 9:
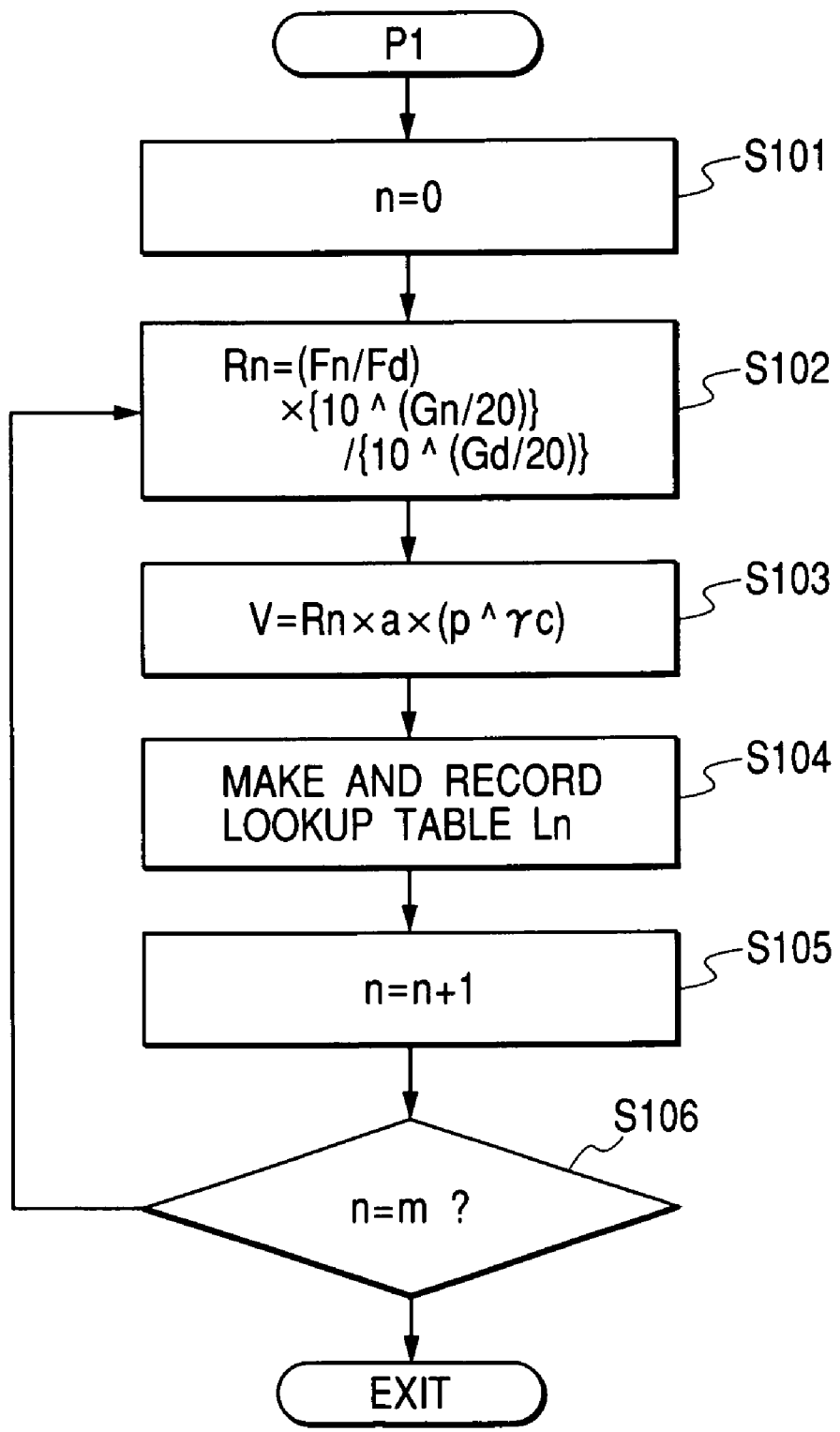
FIG. 9 is a flowchart diagram of a subroutine off FIG. 6.

Using the light intensity Fd and gain Gd of the image Pd and the light intensity Fn and gain Gn of the image Pn read in the memory 82, and γ of the image pickup mean, the CPU 85 of the image process recording means 30 shown in FIG. 5 calculates the correction value Rn using the equation (5) for the m images Pn in the image group So, successively creates a lookup table Ln shown in characteristics 71 (Rn>1) or characteristics 72 (Rn<1) determined by the equation (7) as shown in the flowchart of FIG. 9, and stores the same in the memory 87.

In the flowchart of FIG. 9, the following steps are carried out.

S101: Fist, an initial value n=0 is assigned to n.

S102: Rn is determined according to the equation (5).

S103: V is determined according to the equation (7).

S104: The lookup table Ln is determined and stored in the memory 87.

S105: Next calculation is performed with n=n+1.

S106: The above operations are repeated until n=m.

By the above operations, the lookup table Ln is created.

S005: The lookup table Ln created based on the flowchart of FIG. 9 is used for display of the image Pn to express the image as an image photographed under the intensity Fd of emitted light when the image Pd is photographed and the gain Gd during photographing.

Figure 10:
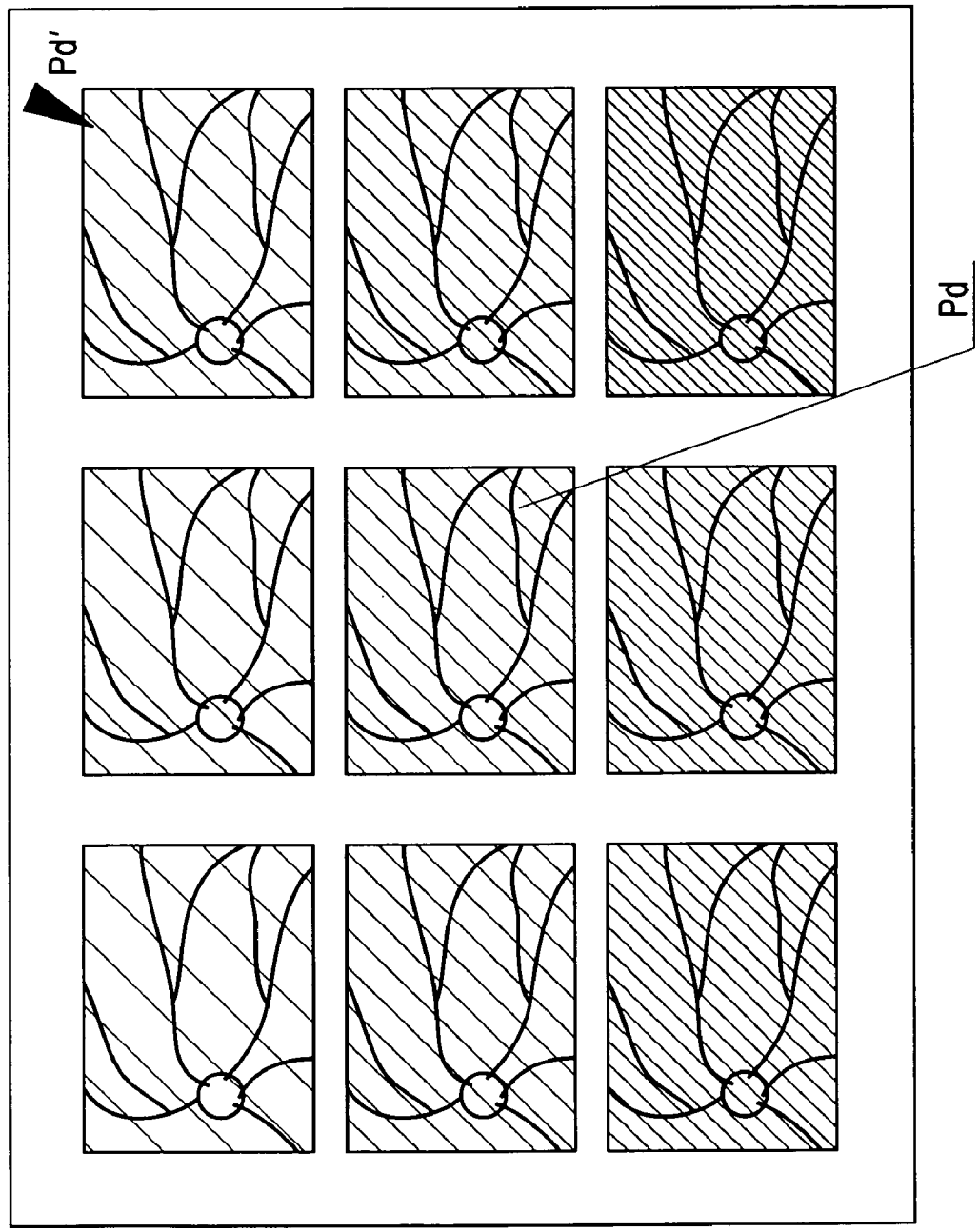
FIG. 10 shows an example of images in the image group So after image processing.

FIG. 10 shows display in the image display means 32 after processing all images in the image group So after being subjected to the above image processing. Images are expressed with different brightness levels with respect to the reference image Ph.

Figure 11:
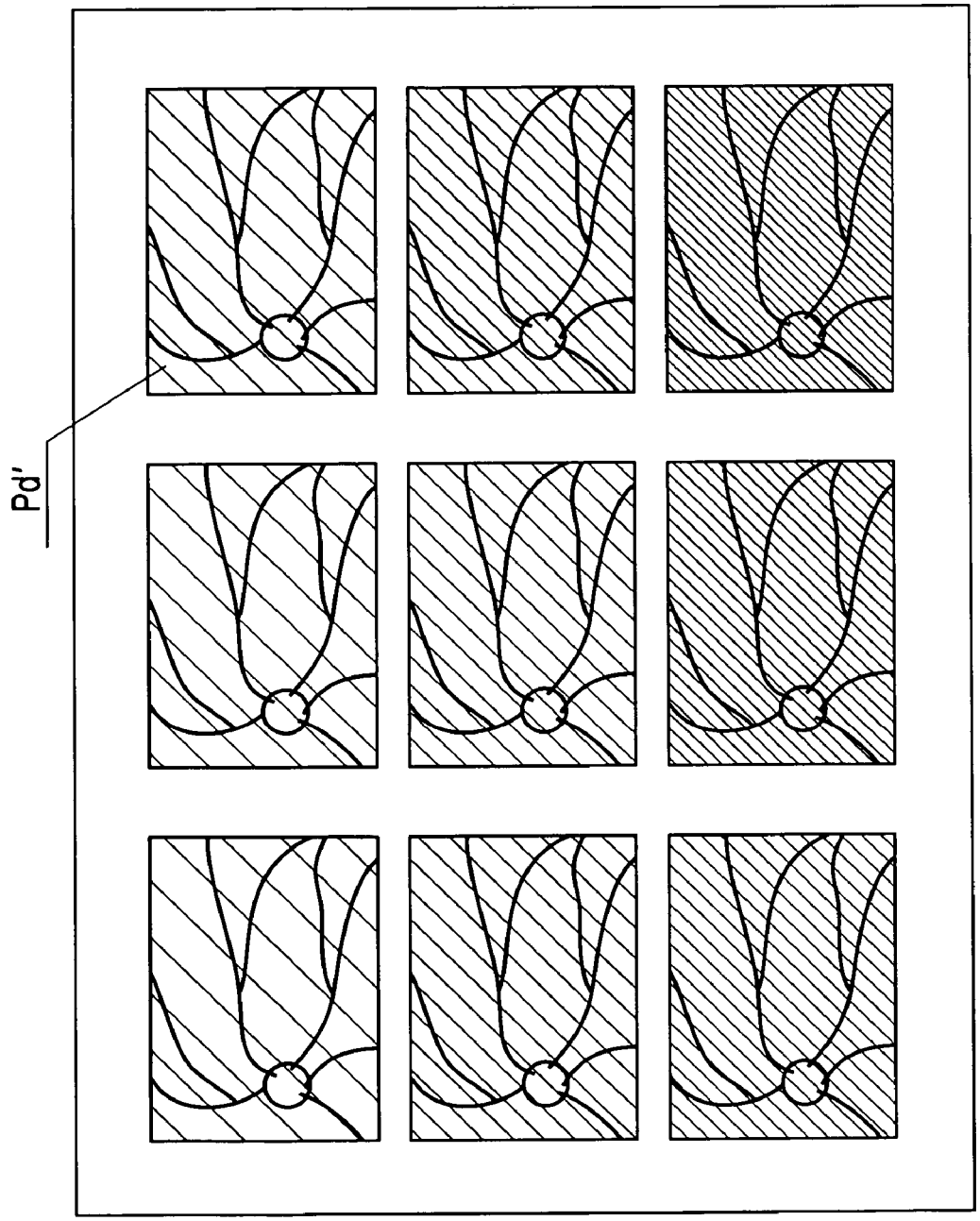
FIG. 11 shows an example display of images in the image group So after changing a reference image.

S006: If an image Pd' other than the image Pd is selected in this state in the same manner as described previously, the reference image is changed from the image Ph to the image Pd', the image processing described previously is newly carried out with the image Pd' as a reference, and display is provided in the image display means 32 as shown in FIG. 11.

Furthermore, for satisfactorily displaying the image distant from the reference image Pd, the right side of the equation (7) is multiplied by a compression factor b (b<1) to obtain the following equation.

$$V = b \times Rn \times a \times (p \char`\^ \gamma c) \qquad (8)$$

A lookup table Ln' shown in characteristics 73 (Rn>1) or characteristics 74 (Rn<1) determined by the equation (8) may be created and used for expression of the image Pn other than the reference image Pd.

In this case, the image is expressed with a difference in brightness of the actual subject compressed, and therefore the shade should be carefully read.

For improving the accuracy of reproduction, the lookup table of the image Pn is subjected to processing for canceling the characteristics of the image pickup means 27, and then a lookup table Ln for display with the result of the processing corrected with the correction value Rn is created.

Figure 12:
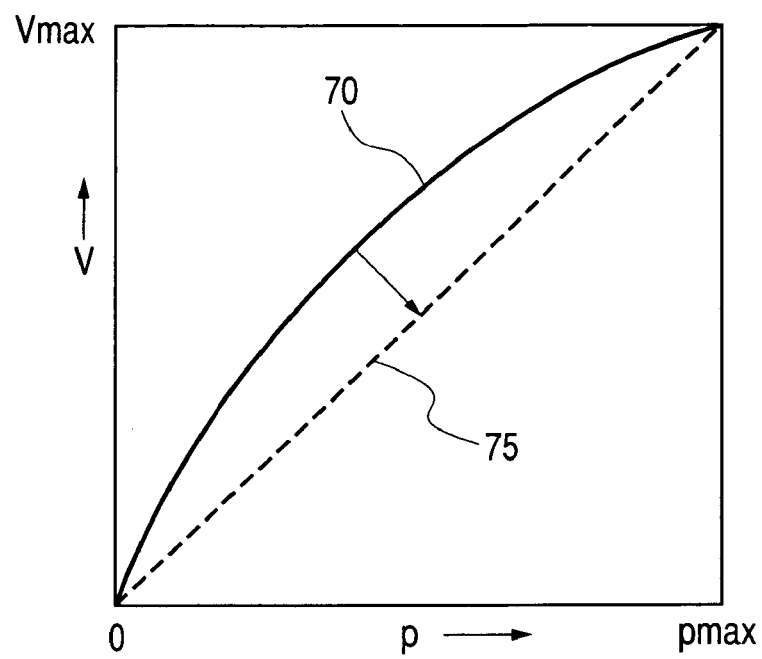
FIG. 12 shows correction of image data to $\gamma=1$.

Image data of the image Pn shown in the lookup table characteristics 70 of FIG. 12 is powered by an inverse of gamma characteristics γc of the image pickup means 27 to correct γ=1 shown in the characteristics 75 for the image data.

Figure 13:
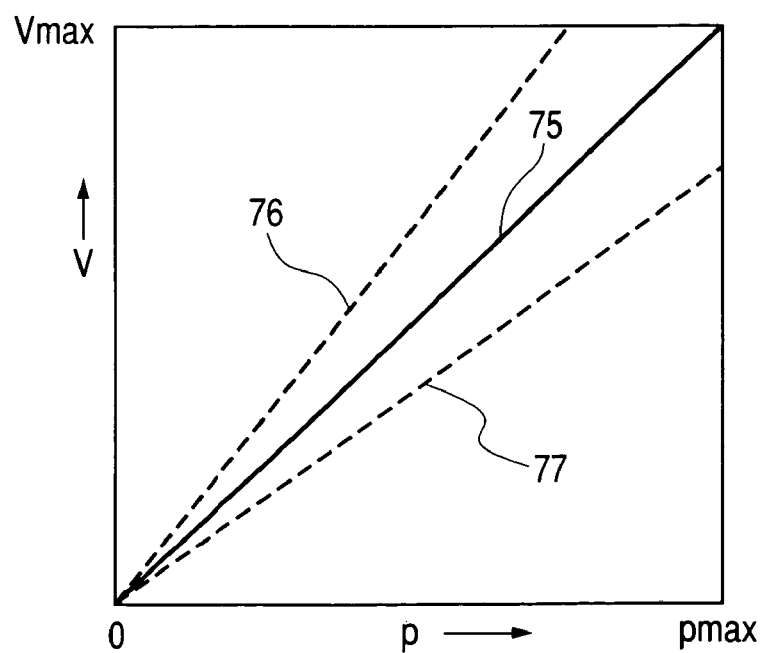
FIG. 13 is a lookup table after correction to $\gamma=1$.

As shown in FIG. 13, the lookup table of the image Pn has characteristics 75. The relation between the input V and the output p in the characteristics 75 is expressed by the following equation:

$$V = p \qquad (9)$$

The right side of the equation (9) is multiplied by the correction value Rn calculated by the equation (5) to obtain the following correction equation.

$$V = Rn \times p \qquad (10)$$

For the image Pn in the image group So, a lookup table Ln shown in the characteristics 76 (Rn>1) or characteristics 77 (Rn<1) determined by the equation (10) is created and used for display of the image Pn.

Further, for improving the accuracy in terms of display, the lookup table is corrected with γ characteristics γm of the display means 32 adapted to the characteristics 76 (Rn>1) or characteristics 77 (Rn<1).

Figure 14:
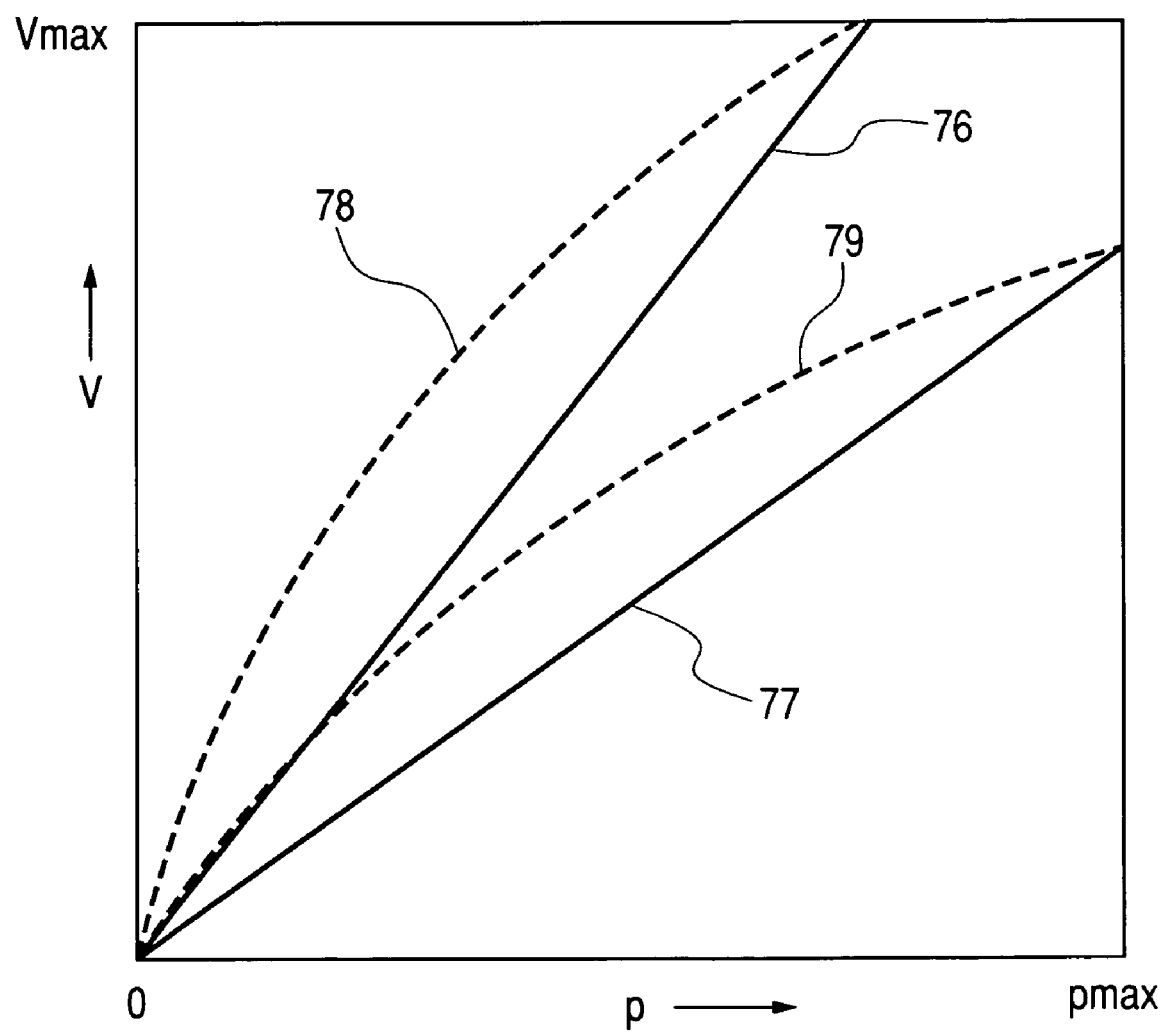
FIG. 14 is a lookup table with gamma characteristics of display means.

For the characteristics 76 (Rn>1) or characteristics 77 (Rn<1) shown in the equation (10) of FIG. 14, p of the right side of the equation (10) is powered by γ characteristics γm of the display means 32 to obtain the following correction equation.

$$V = Rn \times p \char`\^ \gamma m \qquad (11)$$

For the image Pn in the image group So, a lookup table Ln'' shown in characteristics 78 (Rn>1) or characteristics 79 (Rn<1) determined by the equation (11) is created and used for display of the image Pn.

In the above image correction, both the intensity of emitted light and gain are used as parameters, but it is also possible to fix one of the parameters to determine a correction amount with one parameter. In this case, 1 may be assigned to f1 (Fn, Fd) or f2 (Gn, Gd) as necessary.

Other than selecting an image with the touch sensor, an image may be selected with a cursor key or the like provided in the keyboard switch 38, or an image ID may be entered through the keyboard switch 38 to select an image.

Figure 15:
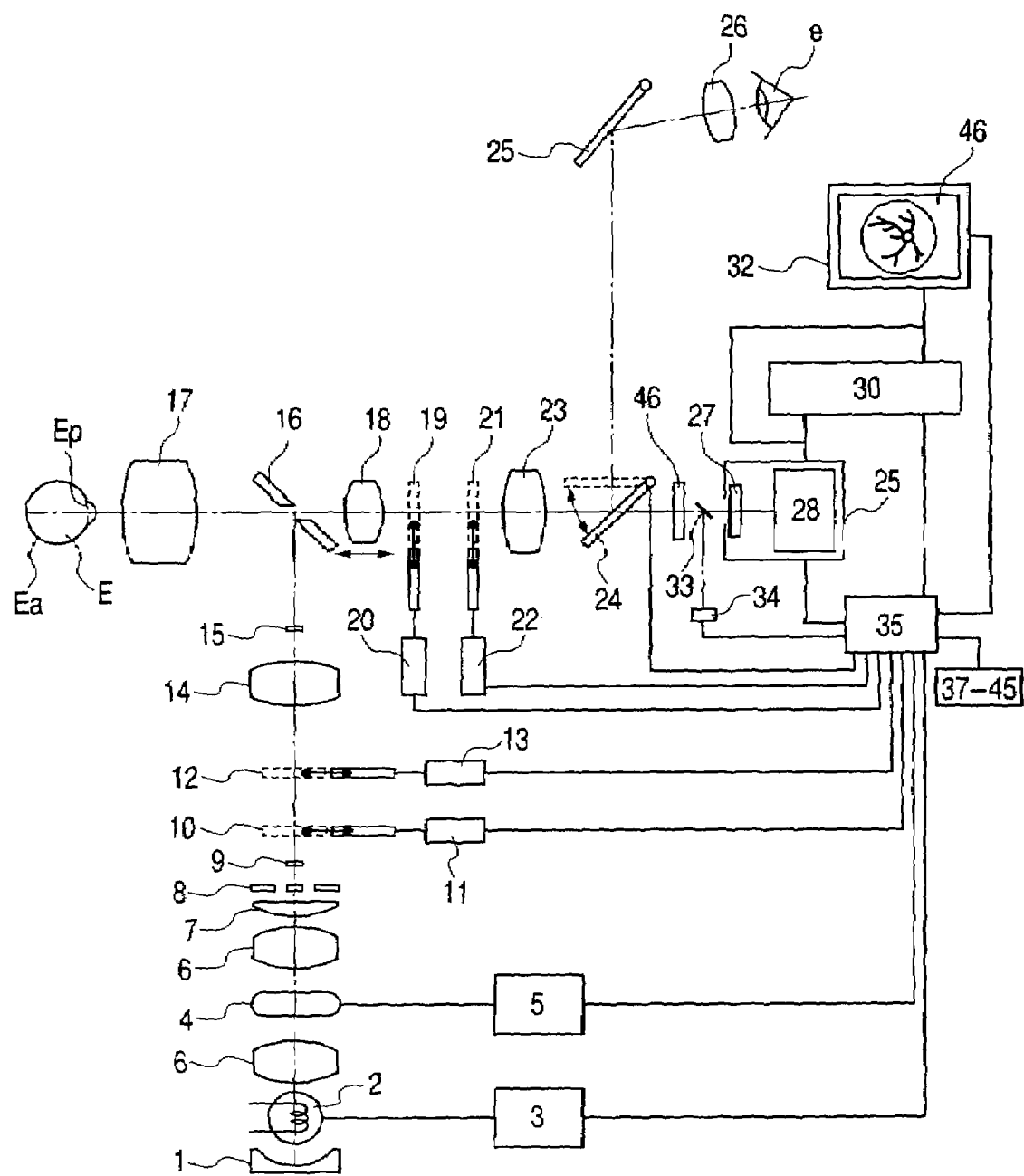
FIG. 15 is a block diagram of the apparatus.

As shown in FIG. 15, a liquid crystal board or a transmittance variable member 47 capable of changing the transmittances of a plurality of selectable ND filters or the like having different transmittances is placed in front of the electronic image pickup means 27, and the member 47 is situated under control by the control means 35. If the transmittance variable member 47 is changed so that the light-exposure value of the electronic image pickup means 29 is an appropriate value, according to the light intensity in the illuminating light system detected from the output of the light intensity sensor 34 by the control means 35, and the electronic image pickup means 27 is configured so that its light exposure value can be adjusted, the member 47 can be used as an alternative or aid for change of the intensity of emitted light of the stroboscopic tube 4 and change of the gain of the image signal amplifying means 28.

In other words, the transmittance can be used as a photographic condition parameter.

The transmittances of the transmittance variable member 47 during photographing of the reference image Pd and any image Pn are determined to be Ed and En, respectively, and as a function for determining a brightness ratio at the light receiving surface of the image pickup element 27 during photographing of the image Pd for the image Pn as described previously, f3 is defined as follows.

If ND is employed as a unit of the transmittance, the intensity of transmitted light when ND=En holds equals $1/(10 \char`\^ En) \times 100$ (%), and thus the function f3 is expressed by the following equation:

$$f3(En, Ed) = (10 \char`\^ En)/(10 \char`\^ Ed) \qquad (8).$$

If the equation (5) is multiplied by this function, the transmittance can be used as a photographic condition parameter.

In the above example, additional information such as the image ID parameter and the photographic condition parameter is added to the image itself and recorded in the image process recording means 30 but, for example, each of the image and additional information of the image can be given the same serial number and separately recorded, called as necessary utilizing the added serial number, and used as integral image information.

The control means 35 can serve also as the CPU 85 of the image process storing means 30.

Furthermore, instead of including the image process storing means 30 and the image display means 32 in the ophthalmologic photographing apparatus, they may be independently provided as the processing apparatus and the display apparatus and electrically connected to the control means 35 of the ophthalmologic photographing apparatus main body to form one ophthalmologic photographing apparatus as a whole as a matter of course.

As described above, in the ophthalmologic apparatus according to the present invention, an image in an optimum exposure state can be obtained by correction of the light exposure value and adjustment of the amplification factor of an image signal using electronic image pickup means having a small latitude (exposure allowable range) even in the photographing of a subject of which the brightness of a photographing object largely changes as in fluorescent contrast photography, while a change in brightness of a fluorescent contrast image with time due to loss of brightness by correction of the light exposure value and adjustment of the amplification factor of the image signal can be visually determined. That is, storage of images, retrieval and convenience of application associated with electronic image photography are added to the diagnostic value of the image obtained with the conventional silver photographed image, resulting in a significant improvement in value of the photographed image.

What is claimed is:

1. An ophthalmologic apparatus comprising:
    image pickup means for picking-up images of an eye to be examined;
    image pickup condition adjusting means for adjusting image pickup conditions for picking-up the images of the eye to be examined;
    storage means for storing the image pickup conditions in relation to the picked up images respectively;
    image correcting means for correcting a display condition of a target image which is not a designated reference image, based on the image pickup condition of the designated reference image and the target image; and
    display control means controls a display of the target image based on the corrected display condition.

2. The ophthalmologic apparatus according to claim 1, wherein said image pick-up conditions include at least one of an image picking-up mode, an amplification factor of the image pick-up means, an intensity of illuminating light for the eye, and an elapsed time from injection of a fluorescent contrast medium to the eye.

3. A method for displaying retinal images photographed by an ophthalmologic apparatus, comprising the steps:
    Step 1: setting a first image pick-up condition, and capturing a first retinal image of an eye to be examined;
    Step 2: storing said first image pick-up condition;
    Step 3: setting a second image pick-up condition after elapse of predetermined time, and capturing a second retinal image of said eye to be examined;
    Step 4: storing said second image pick-up condition;
    Step 5: selecting said first or second retinal image;
    Step 6: comparing the stored image pick-up condition of a selected retinal image with the stored image pick-up condition of the other image;
    Step 7: setting display conditions of the first and second images based on the result of said comparison; and
    Step 8: displaying said first and second images on display means.

4. An image processing apparatus for processing an image picked-up by an ophthalmologic apparatus, comprising:
    a display control unit for controlling a display of images whose image pickup conditions are adjusted by the ophthalmologic apparatus, wherein the image pickup conditions are stored respectively in relation to the images in a memory; and
    a receiving unit for receiving designation of a reference image from the images,
    wherein a display control unit corrects a display condition of a target image which is not a designated reference image, based on the image pickup condition of the designated reference image and the target image, and controls a display of the target image based on the corrected display condition.

5. An image processing method for processing an image picked-up by an ophthalmologic apparatus, comprising the steps of:
    controlling a display of images whose image pickup conditions are adjusted by the ophthalmologic apparatus,
    wherein the image pickup conditions are stored respectively in relation to the images in a memory;
    receiving designation of a reference image from the images; and
    correcting display conditions of a target image which is not a designated reference image, based on the image pickup condition of the designated reference image and the target image; and
    controlling a display of the target image based on the corrected display conditions.

* * * * *